(12) United States Patent
Smith

(10) Patent No.: US 9,492,581 B2
(45) Date of Patent: Nov. 15, 2016

(54) OPHTHALMIC AND CONTACT LENS SOLUTIONS CONTAINING SIMPLE SACCHARIDES AS PRESERVATIVE ENHANCERS

(75) Inventor: Francis X. Smith, Salem, NH (US)

(73) Assignee: FXS VENTURES, LLC, Salem, NH (US)

( * ) Notice: Subject to any disclaimer, the term of this patent is extended or adjusted under 35 U.S.C. 154(b) by 2724 days.

(21) Appl. No.: 10/544,151

(22) PCT Filed: Nov. 8, 2001

(86) PCT No.: PCT/US01/46344
§ 371 (c)(1),
(2), (4) Date: Aug. 1, 2005

(87) PCT Pub. No.: WO02/38161
PCT Pub. Date: May 16, 2002

(65) Prior Publication Data
US 2006/0142169 A1    Jun. 29, 2006

Related U.S. Application Data

(60) Provisional application No. 60/246,870, filed on Nov. 8, 2000.

(51) Int. Cl.
| | | |
|---|---|---|
| *C11D 3/00* | (2006.01) |
| *A61L 12/14* | (2006.01) |
| *A01N 47/44* | (2006.01) |
| *C11D 3/22* | (2006.01) |
| *C11D 3/37* | (2006.01) |
| *C11D 7/26* | (2006.01) |

(52) U.S. Cl.
CPC ............ *A61L 12/142* (2013.01); *A01N 47/44* (2013.01); *A61L 12/143* (2013.01); *A61L 12/145* (2013.01); *C11D 3/0078* (2013.01); *C11D 3/221* (2013.01); *C11D 3/3723* (2013.01); *C11D 7/261* (2013.01)

(58) Field of Classification Search
CPC ................... A01N 47/44; A01N 43/16
See application file for complete search history.

(56) References Cited

U.S. PATENT DOCUMENTS

| | | |
|---|---|---|
| 1,432,345 A | 10/1922 | Lasker |
| 2,976,576 A | 3/1961 | Wichterle et al. |
| 3,428,576 A | 2/1969 | Dickinson et al. |
| 3,429,576 A | 2/1969 | Ikeda |
| 3,503,393 A | 3/1970 | Manley |
| 3,591,329 A | 7/1971 | Chromecek et al. |
| 3,689,673 A | 9/1972 | Phares, Jr. |
| 3,755,561 A | 8/1973 | Rankin |
| 3,873,696 A | 3/1975 | Randeri et al. |
| 3,876,768 A | 4/1975 | Blank |
| 3,888,782 A | 6/1975 | Boghosian et al. |
| 3,910,296 A | 10/1975 | Karageozian et al. |
| 3,911,107 A | 10/1975 | Krezanoski |
| 3,912,450 A | 10/1975 | Boucher |
| 3,943,251 A | 3/1976 | Medow et al. |
| 4,022,834 A | 5/1977 | Gundersen |
| 4,029,817 A | 6/1977 | Blanco et al. |
| 4,046,706 A | 9/1977 | Krezanoski |
| 4,136,173 A | 1/1979 | Pramoda et al. |
| 4,136,175 A | 1/1979 | Rideout et al. |
| 4,136,534 A | 1/1979 | Villa |
| 4,209,817 A | 6/1980 | McGinnis |
| 4,354,952 A | 10/1982 | Reidhammer et al. |
| 4,361,458 A | 11/1982 | Grajek et al. |
| 4,361,548 A | 11/1982 | Smith et al. |
| 4,361,549 A | 11/1982 | Kung et al. |
| 4,394,381 A | 7/1983 | Sherrill |
| 4,439,417 A | 3/1984 | Matsunaga et al. |
| 4,525,346 A | 6/1985 | Stark |
| 4,599,360 A | 7/1986 | Fukami et al. |
| RE32,672 E | 5/1988 | Huth et al. |
| 4,748,189 A | 5/1988 | Su et al. |
| 4,758,595 A | 7/1988 | Ogunbiyi et al. |
| 4,783,488 A | 11/1988 | Ogunbiyi et al. |
| 4,820,352 A | 4/1989 | Reidhammer et al. |
| 4,826,879 A | 5/1989 | Yamamoto et al. |
| 4,836,986 A | 6/1989 | Ogunbiyi et al. |
| 4,863,900 A | 9/1989 | Pollock et al. |
| 4,891,423 A | 1/1990 | Stockel |
| 4,894,454 A | 1/1990 | Paradies |
| 4,988,710 A | 1/1991 | Olney |
| 4,997,626 A | 3/1991 | Dziabo et al. |
| 5,030,721 A | 7/1991 | Kasai et al. |

(Continued)

FOREIGN PATENT DOCUMENTS

| | | |
|---|---|---|
| EP | 0 812 592 A1 | 12/1997 |
| EP | 0 923 950 A3 | 12/2000 |

(Continued)

OTHER PUBLICATIONS

Ballweber et al., "In Vitro Microbicical Activities of Cecropin Peptides D2A21 and D4E1 and Gel Formulations Containing 0.1 to 2% D2A21 against *Chlamydia trachomatis*", Antimicrobial Agents and Chemotheraphy, Jan. 2002, pp. 34-41, vol. 46, No. 1.

(Continued)

*Primary Examiner* — Zohreh Fay
(74) *Attorney, Agent, or Firm* — Peter J. Mikesell; Christopher E. Blank, Esq.; Schmeiser, Olsen & Watts, LLP

(57) ABSTRACT

A contact lens solution comprising 0.001 to 10 weight percent or a preservative enhancer chosen from the group consisting of: inositol; mannitol; sorbitol; sucrose; dextrose; glycerin and propylene glycol; and at least 0.0001 weight percent of a cationic polymeric preservative, and where the concentration of chloride in said solution is less than 0.2 percent by weight.

1 Claim, No Drawings

(56) References Cited

U.S. PATENT DOCUMENTS

| | | |
|---|---|---|
| 5,078,908 A | 1/1992 | Ripley et al. |
| 5,089,261 A | 2/1992 | Nitecki et al. |
| 5,122,354 A | 6/1992 | Tsuji et al. |
| 5,174,872 A | 12/1992 | Scott |
| 5,175,161 A | 12/1992 | Yokoyama et al. |
| 5,182,258 A | 1/1993 | Chiou |
| 5,192,535 A | 3/1993 | Davis et al. |
| 5,279,673 A | 1/1994 | Dziabo et al. |
| 5,300,296 A | 4/1994 | Holly et al. |
| 5,306,440 A | 4/1994 | Ripley et al. |
| 5,361,287 A | 11/1994 | Williamson |
| 5,380,303 A | 1/1995 | Holly et al. |
| 5,439,572 A | 8/1995 | Pankow |
| 5,449,658 A | 9/1995 | Unhoch et al. |
| 5,494,937 A | 2/1996 | Asgharian et al. |
| 5,547,990 A | 8/1996 | Hall et al. |
| 5,591,773 A | 1/1997 | Grunberger et al. |
| 5,607,681 A | 3/1997 | Galley et al. |
| 5,624,958 A | 4/1997 | Isaacs et al. |
| 5,660,862 A | 8/1997 | Park et al. |
| 5,661,130 A | 8/1997 | Meezan et al. |
| 5,674,450 A | 10/1997 | Lin et al. |
| 5,691,379 A | 11/1997 | Ulrich et al. |
| 5,718,895 A | 2/1998 | Asgharian et al. |
| 5,719,110 A | 2/1998 | Cook |
| 5,741,817 A | 4/1998 | Chowhan et al. |
| 5,770,582 A | 6/1998 | von Borstel et al. |
| 5,780,450 A | 7/1998 | Shade |
| 5,807,585 A | 9/1998 | Martin et al. |
| 5,811,446 A | 9/1998 | Thomas |
| 5,854,303 A | 12/1998 | Powell et al. |
| 5,869,468 A | 2/1999 | Freeman |
| 5,888,950 A | 3/1999 | Potini et al. |
| 5,891,733 A | 4/1999 | Inoue |
| 5,925,317 A | 7/1999 | Rogalskyj et al. |
| 5,925,320 A | 7/1999 | Jones |
| 5,925,371 A | 7/1999 | Ishiwatari |
| 5,942,218 A | 8/1999 | Kirschner et al. |
| 5,945,446 A | 8/1999 | Laub |
| 5,965,736 A | 10/1999 | Akhavan-Tafti |
| 5,968,904 A | 10/1999 | Julian et al. |
| 6,001,805 A | 12/1999 | Jaynes et al. |
| 6,008,195 A | 12/1999 | Selsted |
| 6,022,732 A | 2/2000 | Bakhit et al. |
| 6,056,920 A | 5/2000 | Lepre |
| 6,117,869 A | 9/2000 | Picard et al. |
| 6,121,327 A | 9/2000 | Tsuzuki et al. |
| 6,126,706 A | 10/2000 | Matsumoto et al. |
| 6,139,646 A * | 10/2000 | Asgharian et al. ............. 134/42 |
| 6,153,563 A | 11/2000 | Smith et al. |
| 6,153,568 A | 11/2000 | McCanna et al. |
| 6,162,393 A * | 12/2000 | De Bruiju et al. ............. 422/28 |
| 6,191,110 B1 | 2/2001 | Jaynes et al. |
| 6,309,596 B1 | 10/2001 | Xia et al. |
| 6,309,658 B1 | 10/2001 | Xia et al. |
| 6,432,893 B1 | 8/2002 | Doi et al. |
| 6,617,291 B1 | 9/2003 | Smith |
| 6,624,203 B1 | 9/2003 | Smith |
| 2003/0190258 A1 | 10/2003 | Smith |
| 2005/0042198 A1 | 2/2005 | Smith et al. |

FOREIGN PATENT DOCUMENTS

| | | |
|---|---|---|
| GB | 1398058 | 3/1973 |
| JP | 58010517 A | 1/1983 |
| JP | 10-108899 | 4/1998 |
| JP | 2000016965 A | 1/2000 |
| RU | 2127100 | 3/1999 |
| WO | WO 91/01763 | 2/1991 |
| WO | WO 92/04905 | 4/1992 |
| WO | WO 92/11876 | 7/1992 |
| WO | WO 92/21049 | 11/1992 |
| WO | WO 94/00160 | 1/1994 |
| WO | WO 95/00176 | 1/1995 |
| WO | WO 96/06603 | 3/1996 |
| WO | WO 97/34834 | 9/1997 |
| WO | WO 97/41215 | 11/1997 |
| WO | WO 99/23887 | 5/1999 |
| WO | WO 99/37295 | 7/1999 |
| WO | WO 00/07634 | 2/2000 |
| WO | WO 00/11514 | 3/2000 |

OTHER PUBLICATIONS

Creighton, Thomas E., "Proteins Structures and Molecular Properties", W.H. Freeman & Co., New York, 125 1984, pp. 179-182.
De Lucca et al., "Fungicidal Properties, sterol binding, and proteolytic resistance of the synthetic peptide D4E1", Canadian Journal of Microbiology, Jun. 1998, pp. 514-520, vol. 44, No. 6.
Keay. L., Moser, P.W. and Wildo, B.S., "Proteases of the Genus *Bacillus*, II. Alkaline Proteases", Biotechnology & Bioengineering, Mar. 1970, pp. 213-249, vol. XII.
Keay. L. and Moser, P.W., "Differentiation of Alkaline Proteases form *Bacillus* Species", Biochemical and Biophysical Research Comm, 1969, pp. 600-604, vol. 34, No. 5.
Schutte, L., et al., "The Substitution Reaction of Histidine and Some Other Imidazol Derivatives With Iodine", Tetrahedon, Supp. No. 7, 1985, pp. 295-306.

\* cited by examiner

OPHTHALMIC AND CONTACT LENS SOLUTIONS CONTAINING SIMPLE SACCHARIDES AS PRESERVATIVE ENHANCERS

CROSS-REFERENCE TO RELATED APPLICATIONS

This application claims the benefit of U.S. Provisional Patent Application Ser. No. 60/246,870, filed Nov. 8, 2000.

FIELD OF THE INVENTION

The present invention relates to the field of ophthalmic solutions and their uses. In particular the invention relates to contact lens cleaning solutions, contact lens rinsing and storing solutions, solutions to deliver active pharmaceutical agents to the eye, solutions for disinfecting ophthalmic devices and the like.

BACKGROUND

The present invention relates to the field of ophthalmic solutions and especially to the aspects of preservative efficacy and comfort after prolonged use. These ophthalmic solutions have been used for some period of time and are available as over the counter products. Solutions that are used in direct contact with corneal tissue such as the delivery of active pharmaceutical agent to the eye, or indirectly, such as the cleaning, conditioning or storage of devices that will come in contact with corneal tissue, such as contact lenses, there is a need to insure that these solution do not introduce sources of bacterial or other microbial infection. Thus preservatives are included to reduce the viability of microbes in the solution and to lessen the chance of contamination of the solution by the user since many of the solutions are bought, opened, used, sealed and then reused.

State of the art preservative agents include polyhexamethylene biguanide (phmb), POLYQUAD™, chlorhexidine, and benzalkonium chloride, and the like, all of which at some concentration irritate corneal tissue and lead to user discomfort. Therefore, a solution that employs a given amount of a preservative agent, but which is made more effective by addition of an agent that is not a preservative agent would be desired.

SUMMARY OF THE INVENTION

The present invention relates to improved ophthalmic solutions that employ inositol in order to more effectively preserve solutions and to reduce the degree to which cationic preservatives will deposit on contact lenses. Ophthalmic solutions are here understood to include contact lens treatment solutions, such as cleaners, soaking solutions, conditioning solutions and lens storage solutions, as well as wetting solutions and in-eye solutions for treatment of eye conditions.

The solutions specifically described herein have 0.001 to about 1 percent of inositol in combination with other active ingredients useful in ophthalmic solutions such as buffers, preservatives, surfactants, and antimicrobial agents, and with a low chloride concentration, less than about 0.2 percent by weight. It has been found, surprisingly that inositol, and other sugars including mannitol, sorbitol, sucrose, dextrose, glycerin and propylene glycol, effectively increase the antibacterial effect of preservatives in low salt (low chloride) conditions.

The preservatives that are specifically useful are cationic polymeric preservatives such as polyhexamethylene biguanide (phmb), POLYQUAD™, chlorhexidne, and benzalkonium chloride, as well as other cationic preservatives that may prove useful in the present invention as well. The cationic preservatives are used at effective amounts as preservatives, and in the instance of PHMB from 0.0001 percent by weight to higher levels of about 0.01 weight percent. Specifically, the cationic polymeric preservative includes polymeric biguanides such as polymeric hexamethylene biguanides (PHMB), and combinations thereof. Such cationic polymeric biguanides, and water-soluble salts thereof, having the following formula:

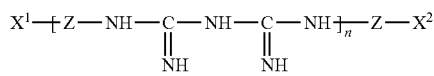

wherein Z is an organic divalent bridging group which may be the same or different throughout the polymer, n is on average at least 3, preferably on average 5 to 20, and $X^1$ and $X^2$ are

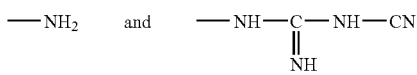

One preferred group of water-soluble polymeric biguanides will have number average molecular weights of at least 1,000 and more preferably will have number average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. No. 3,428,576 describes the preparation of polymeric biguanides from a diamine and salts thereof and a diamine salt of dicyanimide.

Most preferred are the polymeric hexamethylene biguanides, commercially available, for example, as the hydrochloride salt from Zeneca (Wilmington, Del.) under the trademark COSMOCIL™ CQ. Such polymers and water-soluble salts are referred to as polyhexamethylene (PHMB) or polyaminoptopyl biguanide (PAPB). The term polyhexamethylene biguanide, as used herein, is meant to encompass one or more biguanides have the following formula:

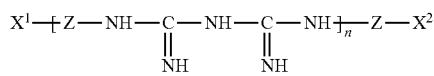

wherein Z, $X^1$ and $X^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated. Preferably, the water-soluble salts are compounds where n has an average value of 2 to 15, most preferably 3 to 12.

It was found that an unexpected preservative efficacy was displayed when inositol was used in conjunction with the cationic preservative. The other components of the solution are used at levels known to those skilled in the art in order to improve the wearability of lenses and when used directly in the eye, to provide increased resistance to infection. Inositol used in ophthalmic solutions increases preservative efficacy in certain formulations, provides increased resistance to infection in corneal tissue, in certain formulations, and improves the quality of tears in certain formulations.

The formulations may also include buffers such as phosphates, bicarbonate, citrate, borate, ACES, BES, BICINE, BIS-Tris, BIS-Tris Propane, HEPES, HEPPS, imidazole, MES, MOPS, PIPES, TAPS, TES, and Tricine.

Surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold by BASF under the trademark CREMOPHOR®.

Inositol, mannitol, sorbitol, sucrose, dextrose, glycerin, propylene glycol and the other agents used in the present invention are all commercially available, and well enough understood to be formulated into products within the scope of the invention by those skilled in the art.

The solutions of the present invention may contain other additives including but not limited to buffers, tonicity agents, demulcents, wetting agents, preservatives, sequestering agents (chelating agents), surface active agents, and enzymes.

Other aspects include adding to the solution from 0.001 to 1 weight percent chelating agent (preferably disodium EDTA) and/or additional microbicide, (preferably 0.00001 to 0.1 or 0.00001 to 0.01) weight percent polyhexamethylene biquanide (PHMB0, N-alkyl-2-pyrrolidone, chlorhexidine, polyquarternium-1, hexetidine, bronopol, alexidine, low concentrations of hydrogen peroxide, and ophthalmologically acceptable salts thereof.

Ophthalmologically acceptable chelating agents useful in the present invention include amino carboxylic acid compounds or water-soluble salts thereof, including ethylenediaminetetraacetic acid, nitrilotriacetic acid, diethylenetriamine pentaacetic acid, hydroxyethylethylenediaminetriacetic acid, 1,2-diaminocyclohexanetetraacetic acid, ethylene glycol bis (beta-aminoethyl ether) in N, N, N', N' tetraacetic acid (EGTA), aminodiacetic acid and hydroxyethylamino diacetic acid. These acids can be used in the form of their water soluble salts, particularly their alkali metal salts. Especially preferred chelating agents are the di-, tri- and tetra-sodium salts of ethylenediaminetetraacetic acid (EDTA), most preferably disodium EDTA (Disodium Edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphates, tetraphosphates, trimetaphosphates, tetrametaphosphates, as well as more highly condensed phosphates in the form of the neutral or acidic alkali metal salts such as the sodium and potassium salts as well as the ammonium salt.

The pH of the solutions should be adjusted to be compatible with the eye and the contact lens, such as between 6.0 to 8.0, preferably between 6.8 to 7.8 or between 7.0 to 7.6. Significant deviations from neutral (pH 7.3) will cause changes in the physical parameters (i.e. diameter) in some contact lenses. Low pH (pH less than 5.5) can cause burning and stinging of the eyes, while very low or very high pH (less than 3.0 or greater than 10) can cause ocular damage.

The additional preservatives employed in the present invention are known, such as polyhexamethylene biguanide, N-alkyl-2-pyrrolidone, chlorhexidine, polyhexamethylenebiguanide, alexidine, polyquaternium-1, hexetidine, bronopol and a very low concentration of hydrogen peroxide, e.g., 30 to 200 ppm.

The solutions of the invention are compatible with both rigid gas permeable and hydrophilic contact lenses during storage, cleaning, wetting, soaking, rinsing and disinfection.

A typical aqueous solution of the present invention may contain additional ingredients which would not affect the basic and novel characteristics of the active ingredients described earlier, such as tonicity agents, surfactants and viscosity inducing agents, which may aid in either the lens cleaning or in providing lubrication to the eye. Suitable tonicity agents include sodium chloride, potassium chloride, glycerol or mixtures thereof. The tonicity of the solution is typically adjusted to approximately 240-310 milliosmoles per kilogram solution (mOsm/kg) to render the solution compatible with ocular tissue and with hydrophilic contact lenses. In one embodiment, the solution contains 0.01 to 0.2 weight percent sodium chloride. The important factor is to keep the concentrations of such additives to a degree no greater than that would supply a chloride concentration of no greater than about 0.2 mole percent.

Suitable viscosity inducing agents can include lecithin or the cellulose derivatives such as hydroxymethylcellulose, hydroxypropylcellulose and methylcellulose in amounts similar to those for surfactants, above.

EXAMPLE 1

Formulations containing inositol (Spectrum) were prepared in a 0.2% phosphate buffer. The solutions were made isotonic with sodium chloride and preserved with polyhexamethylene biquanide at 0.0001%. The pH was adjusted to 7.2 with either 1 N sodium hydroxide or 1 N hydrochloric acid. The in vitro microbicidal activity of the solutions was determined by exposing *C. albicans* to 10 ml of each solution at room temperature for 4 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

| Additive | 4 hour log reduction |
| --- | --- |
| Inositol (0.5%) | 1.1 |
| Buffer control | 0.8 |

The solution containing inositol showed an improvement in the activity against *C. albicans* as compared to the buffer control.

EXAMPLE 2

Formulation Preserved Solution for Rinsing, Storage, Reconstituting Enzyme Tablets A formulation was prepared by dissolving Tricine, Allantoin, Inositol, Disodium edetate, and Polyoxyl 40 Hydrogenated Castor Oil in 80% of the water volume. The pH of the solution was adjusted to 7.3 with 1 N sodium hydroxide. The tonicity of the solution was adjusted with sodium chloride and polyhexamethylene biguanide was added. The solution was diluted to volume with water.

| Constituent | Supplier | % Weight/Volume | Amount |
|---|---|---|---|
| Purified water | | to 80% | 40 mL |
| Tricine | Spectrum | 1.0% | 0.500 g |
| Allantoin | Spectrum | 0.25% | 0.125 g |
| Inositol | Spectrum | 0.1% | 0.050 g |
| Edetate Disodium | Spectrum | 0.055% | 0.0275 g |
| Polyoxyl 40 Hydrogenated Castor Oil | CREMOPHOR ® RH 40 from BASF Co. | 0.1% | 0.5 mL of 10% |
| Sodium Hydroxide, 1N | | as required for pH adjustment to 7.3 | as required for pH adjustment to 7.3 |
| Purified Water | | to 98% | Dilute to 49 mL |
| Sodium Chloride | Fisher | As required for tonicity adjustment 285 mOsm | As required for tonicity adjustment 285 mOsm |
| Polyhexamethylene-biguanide HCl | 20% w/w solution available under the mark COSMOCIL ™ CQ from Avecia | 0.0001% | 50 uL of 0.1% |
| Purified Water | | Balance to 100% | Dilute to 50 mL |

This provides an example of a specific formulation of the present invention but does not fully illustrate the bounds or limits of the invention.

EXAMPLE 3

Sugars and Glycols with Less than 0.1% Chloride

An example of a formulation containing low salt, a buffer and cationic preservative follows:

| Log Reduction | Buffer | Preservative | Preservative Enhancer | Wetting Agent |
|---|---|---|---|---|
| 2.27 | none | PHMB 0.0001% | none | None |
| 3.85 | Bis-Tris Propane 0.2% | PHMB 0.0001% | none | CREMOPHOR ® RH 40 |
| 4.40 | Bis-Tris Propane 0.2% | PHMB 0.0001% | propylene glycol 3% | CREMOPHOR ® RH 40 |
| 4.40 | Bis-Tris Propane 0.2% | PHMB 0.0001% | sorbitol 5% | CREMOPHOR ® RH 40 |
| 4.40 | Bis-Tris Propane 0.2% | PHMB 0.0001% | inositol 5% | CREMOPHOR ® RH 40 |
| 2.98 | OPTI-FREE ® Express | | | |
| 0.68 | Ciba SOLO-Care ® | | | |
| 2.99 | B&L RENU ® MULTIPLUS MPS ® | | | |

Column 1 shows the reduction of c. *albicans* at 4 hours using a typical antibacterial test. The data shows improved activity over the preservative alone; improved activity over the buffer control without sugar additive and improved activity over commercially available products.

EXAMPLE 4

Sugar/Glycol Preservative Efficacy Relationship to Salt Concentration

| Log Reduction | Buffer | Preservative | Additive |
|---|---|---|---|
| 2.53 | none | PHMB 0.0001% | none |
| 1.34 | Bis-Tris Propane 0.2% | PHMB 0.0001% | sodium chloride 0.5% |
| 3.42 | Bis-Tris Propane 0.2% | PHMB 0.0001% | glycerin 0.5% |
| 2.73 | Bis-Tris Propane 0.2% | PHMB 0.0001% | propylene glycol 0.5% |
| 1.13 | Bis-Tris Propane 0.2% | PHMB 0.0001% | potassium chloride 0.5% |
| 3.92 | Bis-Tris Propane 0.2% | PHMB 0.0001% | sorbitol 0.5% |
| 3.23 | Bis-Tris Propane 0.2% | PHMB 0.0001% | mannitol 0.5% |
| 3.06 | Bis-Tris Propane 0.2% | PHMB 0.0001% | inositol 0.5% |
| 3.72 | Bis-Tris Propane 0.2% | PHMB 0.0001% | dextrose 0.5% |

This data shows that the antimicrobial activity of buffer with the sugar or glycol is greater than the preservative alone and that decreased activity at 0.5% sodium chloride or 0.5% potassium chloride solutions occurs as well. Thus the surprising effect of the sugar derived preservative enhancers is displayed and the effects relationship to chloride concentration is demonstrated.

EXAMPLE 5

Solutions with Less than 0.1% Chloride Specifically Using Glycerin

Solutions with a cationic polymeric preservative (PHMB) sodium chloride and glycerin and a buffer were made as shown in the following table and the preservative efficacy was measured.

| Log Reduction | Buffer | Preservative | Sodium Chloride | Glycerin |
|---|---|---|---|---|
| 1.69 | none | PHMB 0.0001% | none | none |
| 1.74 | none | PHMB 0.0001% | 0.1% | none |
| 1.46 | none | PHMB 0.0001% | 0.2% | none |
| 0.86 | none | PHMB 0.0001% | 0.4% | none |
| 0.49 | none | PHMB 0.0001% | 0.5% | none |
| 2.44 | Bis-Tris Propane 0.2% | PHMB 0.0001% | none | none |
| 1.89 | Bis-Tris Propane 0.2% | PHMB 0.0001% | 0.1% | none |
| 1.54 | Bis-Tris Propane 0.2% | PHMB 0.0001% | 0.2% | none |
| 0.98 | Bis-Tris Propane 0.2% | PHMB 0.0001% | 0.4% | none |
| 0.89 | Bis-Tris Propane 0.2% | PHMB 0.0001% | 0.5% | none |
| 2.46 | Bis-Tris Propane 0.2% | PHMB 0.0001% | none | 0.20% |
| 2.41 | Bis-Tris Propane 0.2% | PHMB 0.0001% | none | 0.50% |

The above date illustrates the effect of sodium chloride on preservative efficacy and the effect of glycerin in improving preservative efficacy in low salt solutions.

EXAMPLE 6

Experiment Showing Preservative Effect Inhibition is Buffer Dependent

Solutions were made according to methods described supra with sodium phosphate as the buffer.

| Log Reduction | Buffer | Preservative | Tonicity Agent |
|---|---|---|---|
| 0.79 | Sodium Phosphate 0.2% | PHMB 0.0001% | none |
| 0.33 | Sodium Phosphate 0.2% | PHMB 0.0001% | Sodium Chloride 0.7% |

This data illustrates the problem with sodium chloride is independent of buffer type.

EXAMPLE 7

The Lens Conditioning Properties of Saccharide Containing Formulations

Solutions were formulated with sodium chloride, sorbitol and sucrose and then lenses were immersed in the resultant solutions and chlorohexidine gluconate was added. The lenses were exposed for 3 hours and the amount of the chlorohexidine deposited on the lens was measured.

| Method: | HPLC analysis for chlorhexidine gluconate 3.0 mL solution exposed to ½ lens |
|---|---|
| Matrix: | 1 ppm CHG/0.2% Bis-Tris Propane/0.1% CREMOPHOR ® RH 40 |
| Lens: | Freshlook ColorBlends (45% phemfilcon A, 55% water) Wesley Jess |

| Additive | ug CHG per lens | % Decrease |
|---|---|---|
| None | 4.0 | 67.3% |
| Sodium Chloride | 3.6 | 59.3% |
| Sorbitol | 3.0 | 50.7% |
| Sucrose | 1.3 | 21.4% |
| 1 ppm CHG Std in water | % RSD through the entire experiment | 2.9% |

This test shows that the sugars used in the test have an ability to decrease the extent of preservative binding for of cationic preservatives when properly formulated. Both sorbitol and sucrose solutions demonstrated efficacy in reducing preservative deposition.

EXAMPLE 8

The following experiment demonstrates the effect of chloride concentration on the antimicrobial effectiveness of PHMB preservative solutions.

| Log Reduction | Buffer | Preservative | NaCl | Additive | Effect |
|---|---|---|---|---|---|
| 1.05 | Bis-Tris 0.2% | PHMB 0.0001% | none | none | 54% |
| 1.47 | Bis-Tris 0.5% | PHMB 0.0001% | none | none | 75% |
| 0.77 | Bis-Tris 0.2% | PHMB 0.0001% | 0.70% | none | 39% |
| 2.39 | Bis-Tris Propane 0.2% | PHMB 0.0001% | none | none | 123% |
| 2.32 | Bis-Tris Propane 0.5% | PHMB 0.0001% | none | none | 119% |
| 0.91 | Bis-Tris Propane 0.2% | PHMB 0.0001% | 0.70% | none | 47% |
| 1.27 | Tricine 0.2% | PHMB 0.0001% | none | none | 65% |
| 1.31 | Tricine 0.5% | PHMB 0.0001% | none | none | 67% |
| 0.62 | Tricine 0.2% | PHMB 0.0001% | 0.70% | none | 32% |

What is claimed is:

1. A method for providing an ophthalmic solution comprising:
   contacting an eye with a single-part solution comprising 0.001 to 10 weight percent of a preservative enhancer chosen from the group consisting of: inositol; mannitol; sorbitol; sucrose; dextrose; and glycerin; at least 0.0001 weight percent of polyhexamethylene biguanide; and where the concentration of chloride in said solution is less than 0.2 percent by weight.

* * * * *